Oct. 28, 1969 W. FLEMER III Plant Pat. 2,936
OAK TREE
Filed Dec. 5, 1967
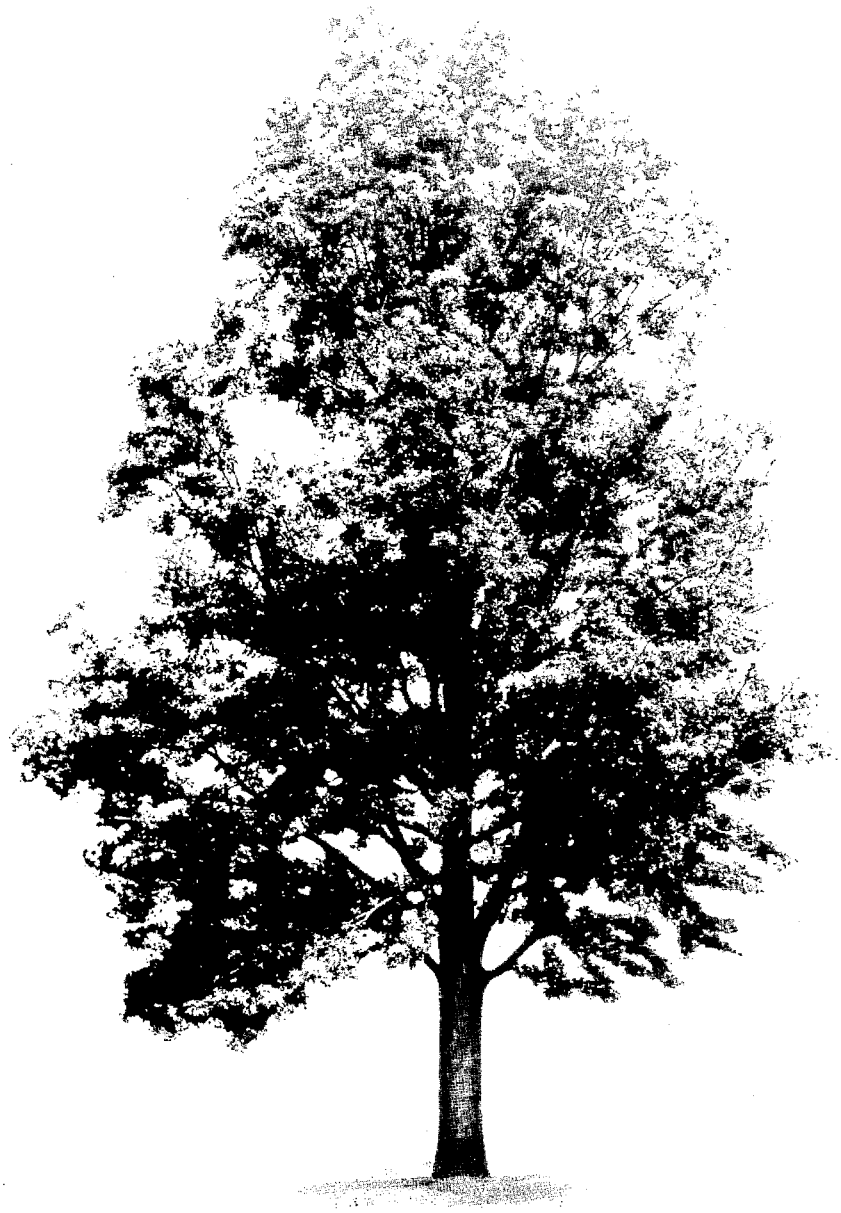
Inventor.
William Flemer, III.
By: Robb & Robb
Attorneys.

United States Patent Office

Plant Pat. 2,936
Patented Oct. 28, 1969

2,936
OAK TREE

William Flemer III, Princeton, N.J., assignor to Treesearch, Kingston, N.J., a partnership Filed Dec. 5, 1967, Ser. No. 688,278
Int. Cl. A01h 5/12
U.S. Cl. Plt.—51 1 Claim The present invention relates to a new and distinct variety of oak tree resembling the species botanically known as *Quercus palustris,* which was originated by me by crossing an unnamed and unpatented variety of oak tree derived from a former cross of an unnamed and unpatented variety of *Quercus palustris*×the *Quercus coccinea* variety known as "Rutherford" (unpatented), with an unnamed and unpatented *Quercus palustris,* the former being the seed parent and the latter being the pollen parent. The variety "Rutherford" has never been introduced in commerce or published, but was apparently of hybrid origin, with a very upright habit, but difficult to propagate. I have found it useful for breeding stock and its name has primarily signified its point of geographic origin.

As the result of this breeding, I have produced a new and improved variety of oak tree which is distinguished from its parents, as well as from all other varieties of which I am aware, as evidenced by the following unique combination of characteristics which are outstanding therein:

(1) A general resemblance to the pin oak with respect to leaf size and shape, fall color and easy transplanting ability;

(2) Upright branches which join the main trunk at a more uniformly acute angle;

(3) Complete absence of objectionable "weeping" or pendant lower branches commonly characteristic to ordinary seedling pin oak trees; and (4) Exceptional hardiness to temperatures as low as −20° F., with freedom from injury by sudden low winter temperatures when other upright pin oak varieties are often badly split on the south sides of their trunks when grown adjacent thereto under the same conditions in the area of New Jersey.

Asexual reproduction of my new variety by grafting, as performed by me in Plainsboro Township, N.J., shows that the foregoing characteristics and distinctions come true and are established and transmitted through succeeding propagations.

The accompanying drawing shows a typical specimen tree of my new oak variety as depicted in black-and-white to illustrate its general form and habit of growth.

The following is a detailed description of my new variety, with color terminology in accordance with the Munsell Color Chart:

Parentage: Seedling.
- *Seed parent.*—An unnamed oak tree variety derived from an unnamed variety of *Quercus palustris* ×the *Quercus coccinea* variety "Rutherford."
- *Pollen parent.*—An unnamed variety of *Quercus palustris.*

Propagation: Holds its distinguishing characteristics through succeeding propagations by grafting.

Locality where grown and observed: Plainsboro Township, N.J.

Tree: Large; upright; tall (illustrated specimen about 40 feet tall and about 20 years old); growth rate substantially the same as that of common grafted pin oaks; hardy to as low as −20° F.
- *Trunk.*—Slender; rough; mature bark color near moderate Olive Brown, Hue 2.5Y 4/4.
- *Branches.*—Slender; smooth. Color—Olive Brown, Hue 7.5Y 3/1.
- *Lenticels.*—Sparse.

Foliage: Very similar to foliage of common pin oaks.
- *Leaves.*—Moderate abundance; from 17 to 19 cm. long (excluding petiole); from 12 to 15 cm. wide; lobed (9 major lobes); deeply incised, with sinuses converging toward their base; cuneate at base; apices bristle-pointed; thick; very lustrous on upper surface. Color—Bright Yellow-Green, Hue 5GY 5/6, changing to Dark Red, Hue 5R 3/7 in the fall. Margin—crenate toward base; serrate at terminals of lobes; smooth edge in sinuses; lobed (9 major lobes and 10 minor lobes). Petiole—medium length (from 3 cm. to 3.5 cm. long). Glands—none. Stipules—none.

Leaf buds:
- *Shape.*—Ovate.
- *Color.*—Moderate Reddish Brown, Hue 10R 3/4.

Flower buds: Concealed.

Flowers: Not significant.

Fruit: Flat cupped acorns about 1.5 cm. wide and 1.4 cm. deep; acorns recessed from about ⅕ to ⅙ of their depth in shallow cups.
- *Borne.*—During October.
- *Abundance.*—Sparse.

General Observations: My new variety is more uniformly upright in habit, with its branches ranging at an acute angle of from 30° to 60° relative to the central leader, and has superior winter-hardiness, particularly with respect to resistance to sudden intense cold temperatures following prolonged warm weather which causes the bark of other common pin oak trees and that of the variety known as "Sovereign" (Plant Patent No. 2,662) to split and form unsightly scars, while trees of my new variety growing under the same conditions and in the same nursery fields in New Jersey have not been adversely affected and remain unharmed.

I claim:

1. A new and distinct variety of oak tree, substantially as herein shown and described, characterized particularly as to novelty by the unique combination of a general resemblance to the pin oak with respect to leaf size and shape, fall color and easy transplanting ability, upright branches which join the main trunk at a more uniformly acute angle, complete absence of objectionable "weeping" or pendant lower branches commonly characteristic of ordinary seedling pin oak trees, and exceptional hardiness to temperatures as low as −20° F., with freedom from injury by sudden low winter temperatures when other upright pin oak varieties are often badly split on the south sides of their trunks when grown adjacent thereto under the same conditions in the area of New Jersey.

No references cited.

ROBERT E. BAGWILL, Primary Examiner